US007025980B1

(12) United States Patent
Williams et al.

(10) Patent No.: US 7,025,980 B1
(45) Date of Patent: Apr. 11, 2006

(54) POLYHYDROXYALKANOATE COMPOSITIONS FOR SOFT TISSUE REPAIR, AUGMENTATION, AND VISCOSUPPLEMENTATION

(75) Inventors: Simon F. Williams, Sherborn, MA (US); David P. Martin, Arlington, MA (US)

(73) Assignee: Tepha, Inc., Cambridge, MA (US)

( * ) Notice: Subject to any disclaimer, the term of this patent is extended or adjusted under 35 U.S.C. 154(b) by 797 days.

(21) Appl. No.: 09/661,773

(22) Filed: Sep. 14, 2000

Related U.S. Application Data

(60) Provisional application No. 60/153,810, filed on Sep. 14, 1999.

(51) Int. Cl.
*A61F 2/02* (2006.01)

(52) U.S. Cl. ....................................... 424/423; 523/113
(58) Field of Classification Search ................. 435/135; 424/422, 423
See application file for complete search history.

(56) References Cited

U.S. PATENT DOCUMENTS

| | | | |
|---|---|---|---|
| 4,664,655 | A | 5/1987 | Orentreich et al. |
| 4,758,234 | A | 7/1988 | Orentreich et al. |
| 4,938,763 | A | 7/1990 | Dunn et al. |
| 5,204,382 | A | 4/1993 | Wallace et al. |
| 5,278,201 | A | 1/1994 | Dunn et al. |
| 5,278,202 | A | 1/1994 | Dunn et al. |
| 5,489,470 | A | 2/1996 | Noda |
| 5,502,116 | A | 3/1996 | Noda |
| 5,563,239 | A | 10/1996 | Hubbs et al. |
| 5,709,854 | A | 1/1998 | Griffith-Cima et al. |
| 5,728,752 | A | 3/1998 | Scopelianos et al. |
| 5,824,333 | A | 10/1998 | Scopelianos et al. |
| 6,277,413 | B1 * | 8/2001 | Sankaram ................ 424/501 |

FOREIGN PATENT DOCUMENTS

| | | | |
|---|---|---|---|
| EP | 0 432 443 | | 6/1991 |
| WO | WO91/13207 | * | 9/1991 |
| WO | 94/02184 | | 2/1994 |
| WO | WO96/00263 | * | 1/1996 |
| WO | 96/21427 | | 7/1996 |
| WO | 96/40304 | | 12/1996 |
| WO | 98/51812 | | 11/1998 |
| WO | WO 98/51812 | * | 12/1998 |
| WO | 99/11196 | | 3/1999 |
| WO | 99/32536 | | 7/1999 |
| WO | WO 99/32536 | * | 7/1999 |
| WO | 00/51662 | | 9/2000 |
| WO | 00/56376 | | 9/2000 |

OTHER PUBLICATIONS

Agostini, et al., "Synthesis and Characterization of Poly-β-Hydroxybutyrate. I. Synthesis of Crystalline DL Poly-β-Hydroxybutyrate from DL-β-Butyrolactone," *Polym. Sci.* Part A-1, 9:2775-2787 (1971).
Byrom, "Miscellaneous Biomaterials," in *Biomaterials*(D. Byrom, ed.) pp. 333-359 (MacMillan Publishers, London 1991).
De Koning et al., *Polymer*35:2090-97 (1994):.
De Smet, et al., "Characterization of Intracellular inclusions formed by Pseudomonas oleovorans during growth on octane,"*J.Bacteriol*.154:870-78 (1983).
Dubois, et al., "Macromolecular Engineering of polylactones and Polylactides. 12. Study of the Depolymerization Reactions of Poly (ε-caprolactone) with Functional Aluminum Alkoxide End Groups,"*Macromolecules* 26:4407-12 (1993).
Gagnon, et al., *Polymer*35:4358-67 (1994).
Gagnon, et al., *Polymer*35:4368-75 (1994).
Gross, et al., "Polymerization if β-monosubstituted-b-propiolactones using trialkylaminimum-water catalytic systems and polymer characterization,"*Macromolecules*21:2657-2668 (1988).
Hocking & Marchessault, "Syndiotactic poly[(R,S)-β-hydroxybutyrate] isolated from methyaluminoxane-catalyzed polymerization,"*Polym. Bull*.30:163-170 (1993).
Hocking & Marchessault, "Biopolyesters"Griffin, Ed., "Chemistry and Technology of Biodegradable Polymers," pp.48-96 (Chapman and Hall, London, 1994).
Holmes, "Biologically Produced (R)-3-hydroxyalkanoate Polymers and Copolymers," in Bassett Ed., "Developments in Crystalline polymers," pp. 1-65 (Elsevier, London, vol. 2., 1988).

(Continued)

*Primary Examiner*—Carlos A. Azpuru
(74) *Attorney, Agent, or Firm*—Pabst Patent Group LLP

(57) ABSTRACT

Polyhydroxyalkanoate materials are provided which are suitable for repair of soft tissue, augmentation, and as viscosupplements in animals, particularly humans. The materials comprise liquid polyhydroxyalkanoate polymer compositions or polyhydroxyalkanoate microdispersions. Devices also are provided for storage and delivery of the polyhydroxyalkanoate compositions in vivo. Methods are provided for repairing or augmenting soft tissue in animals using the materials. In a preferred embodiment, the method include the steps of (a) selecting the animal soft tissue to be repaired or augmented; and (b) placing an injectable, liquid polyhydroxyalkanoate polymer or a polyhydroxyalkanoate microdispersion into the animal soft tissue, preferably using a minimally-invasive method such as injection. In another embodiment, the liquid polyhydroxyalkanoate polymer compositions or polyhydroxyalkanoate microdispersions are used as viscosupplements.

18 Claims, No Drawings

OTHER PUBLICATIONS

Hori, et al., "Ring-Opening Copolymerization of Optically Active β-Butyrolactone with Several Lactones Catalyzed by Distannoxane Complexes: Synthesis of New Biodegradable Polyesters,"*Macromolecules*26:4388-4390 (1993).

Hori, et al., "Ring-Opening Polymerization of Opticallly Active β-Butyrolactone Using Distannoxane Catalysts: Synthesis of High Molecular Wright Poly(3-hydroxybutyrate),"*Macromolecules*26:5533-5534 (1993).

Kemnitzer, et al., "Preparation of predominantly Syndiotactic Poly(β-hydroxybutyrate) by the Tributylin Methoxide Catalyzed Ring-Opening Polymerization of racemicβ-Butyrolactone,"*Macromolecules*26:1221-1229 (1993).

Koosha, "Preparation and characterization of blodegradable polymeric drug carriers,"Ph.D. Disseration, 1989, Univ. Nottingham, UK., *Diss. Abstr. Int. B*51:1206 (1990).

Lafferty et al., "Microbial Production of Poly-β-hydroxybutyric acid," Rehm and Reed, Eds., "Biotechnology"Vertagsgesellschaft, Weinheim, vol. 66, 1988, pp. 135-176.

Le Borgne & Spassky, "Stereoelective polymerization of β-butyrolactone,"*Polymer*30:2312-2319 (1989).

Lemoigne and Roukhelman, "Fermetation β-Hydroxybutyrique Caracterisation et Evolution Des Produits de Deshydration et de Polymerisation de L'acide β-dehydroxybutyrique,"*Annales des fermentations,* 5:527-36 (1925).

Madison & Huisman, "Metabolic engineering of poly(3-hydroxyalkanoates): from DNA to plastic,"*Microbiol. Mol. Biol. Rev.*63:21-53 (1999).

Muller & Seebach, "poly(hydroxyalkanoates): A Fifth Class of Physiologically Important Organic Biopolymers,"*Angew. Chem. Int. Ed. Engl.*32:477-502 (1993).

Poutin & Akhtar, "Biosynthetic polyhydroxyalkanoates and their potential in drug delivery."*Advanced Drug Delivery Reviews*18:133-162 (1996).

Steinbuchel, et al., "A Pseudomones strain accumulating polyesters of 3-hydroxybutyric acid and medium-chain-length 3-hydroxyalkanoic acids,"*Appl. Microbiol. Biotechnol.*37:691-97 (1992).

Steinbuchel, "Polyhydroxyalkanoic Acidds," in Byrom ed., "Biomaterials" MacMillan Publishers, London, 1991, pp.123-213.

Tanahashi & Doi, "Thermal Properties and Stereoregularity of Poly(3-hydroxybutyrate) Prepared from optically Active βButyrolactone with a Zinc-Based Catalyst,"*Macromolecules*24:5732-5733 (1991).

Wallen and Rohwedder, "Poly-β-hydroxyalakaonate from Activated Sludge,"*Environ. Sci Technol.*8:576-79(1974).

Williams & Peoples, "Biodegradable plastics from plants,"*Chemtech*26:38-44 (1996).

Williams & Peoples, "Making Plastics Green,"*Chem. Br.*33:29-32 (1997).

Williams, et al., "PHA applications: addressing the price performance issue I. Tissue engineering,"*Int J. Biol. Macromol.*25:111-121 (1999).

XIE, et al., "Ring-opening Polymerization of β-butyrolactone by Thermophilic Lipases,"*Macromolecules*30:6997-6998 (1997).

* cited by examiner

POLYHYDROXYALKANOATE COMPOSITIONS FOR SOFT TISSUE REPAIR, AUGMENTATION, AND VISCOSUPPLEMENTATION

CROSS-REFERENCE TO RELATED APPLICATIONS

Priority is claimed to U.S. provisional application Ser. No. 60/153,810, filed Sep. 14, 1999.

BACKGROUND OF THE INVENTION

The present invention generally relates to injectable liquid forms or microdispersions of polymers suitable for use in soft tissue repair, augmentation, and as viscosupplements.

A variety of different materials have been used to repair or augment soft tissue defects or to contour abnormalities caused by facial defects, acne, surgical scarring, trauma or aging. Unfortunately, none of these materials is considered to be ideal owing to short-comings in effectiveness or efficacy. For example, liquid silicone was often used to correct soft tissue defects. However, this material was subsequently banned by the FDA when it was discovered that it could migrate to distant parts of the body and cause physiological and clinical problems. Another material, bovine collagen, became available in the 1970's and appeared to be an effective material for treating soft tissue defects. Over time, however, it was discovered that this material was fairly rapidly absorbed. The rapid resorption was partially solved by crosslinking the collagen to extend its lifetime to six months; however, frequent injections of the material are still required. Furthermore, allergic reactions due to bovine proteins present in the collagen persist in the cross-linked material.

A number of newer materials for soft tissue or augmentation have been described. Ceramic particles of calcium phosphate mixed with an aqueous gel carrier in a viscous polymer have been described in U.S. Pat. No. 5,204,382 to Wallace et al. However, there appear to be risks associated with the use of these nonabsorbable particulate materials relating to their migration in vivo. Polymers in combination with solvents and a thermosetting material with a curing agent have both been proposed by Dunn in U.S. Pat. Nos. 4,938,763; 5,278,201; and 5,278,202, but the solvents necessary to dissolve the polymers appear to be less than acceptable, and the materials have limited utility in filling soft tissue defects because they solidify. Furthermore, these materials and other similar commercial materials have ultimate yield stresses close to 10,000 psi compared to between 500 and 2,000 psi for human skin, raising pulpability concerns and making them too hard for repair of soft tissue and especially for dermal augmentation or repair. Other polymer blends based on lactic acid polymers also have been suggested in U.S. Pat. No. 4,235,312 to Buchholz.

Other materials for injection, which solidify to serve as bulking agents or as matrices for tissue ingrowth, are described in U.S. Pat. No. 5,709,854 to Vacanti, et al., and PCT/US96/09065 by Reprogenesis. Exemplary materials in the '854 patent include alginate solutions which are mixed with calcium ions to induce crosslinking after injection. The PCT application discloses alternative crosslinkable synthetic polymers which have similar properties upon exposure to light or multivalent ions.

In this case, however, the polymers are considered to be too viscous to be injected through a needle, which significantly limits their utility. Furthermore, the oligomers also may be slightly soluble in body fluids, facilitating a rapid diffusion out of the site of implantation. To address these concerns, U.S. Pat. Nos. 5,728,752 and 5,824,333 to Scopelianos et al., disclose polymers derived from $\epsilon$-caprolactone, trimethylene carbonate, and/or ether lactones with glycolide, lactide and p-dioxanone units, for use in the repair of soft tissues and augmentation which have lower viscosities and do not harden after implantation. While these compositions appear to have such desirable properties, these materials are fairly rapidly degraded and therefore would need to be re-injected at frequent intervals. Moreover, some of these polymers break-down to monomers well known to cause undesirable inflammatory responses in vivo.

It is therefore an object of the present invention to provide polymeric materials for soft tissue repair and augmentation that are safe, injectable, long lasting, bioabsorbable, and biocompatible.

It is a further object of this invention to provide methods for preparing and using such materials.

SUMMARY OF THE INVENTION

Polyhydroxyalkanoate materials are provided which are suitable for repair of soft tissue, augmentation, and as viscosupplements in animals, particularly humans. The materials comprise liquid polyhydroxyalkanoate polymer compositions or polyhydroxyalkanoate microdispersions. Devices also are provided for storage and delivery of the polyhydroxyalkanoate compositions in vivo.

Methods are provided for repairing or augmenting soft tissue in animals using the materials. In a preferred embodiment, the method include the steps of (a) selecting the animal soft tissue to be repaired or augmented; and (b) placing an injectable, liquid polyhydroxyalkanoate polymer or a polyhydroxyalkanoate microdispersion into the animal soft tissue, preferably using a minimally-invasive method such as injection. In another embodiment, the liquid polyhydroxyalkanoate polymer compositions or polyhydroxyalkanoate microdispersions are used as viscosupplements.

DETAILED DESCRIPTION OF THE INVENTION

It was discovered that polyhydroxyalkanoate polymers can be selected and/or rendered are suitable for use in soft tissue repair, augmentation, and as viscosupplements. In preferred embodiments, these polyhydroxyalkanoate polymer compositions have low viscosities which enable them to be injected into soft tissue or the knee joint with a syringe and needle. These polymers preferably do not harden after implantation. Degradation rates can be controlled so that certain compositions are slow to bioabsorb, thereby decreasing considerably the frequency with which the composition must be re-injected.

I. The Polyhydroxyalkanoate Compositions

The composition comprises a fluid material which comprises a polyhydroxyalkanoate. The polyhydroxyalkanoate is either in the form of a liquid or a microdispersion, and optionally may further include agents to increase the safety and efficacy of the composition. The PHA must be a fluid at body temperature or must be in the form of a microdispersions in a fluid carrier.

As used herein, the term "body temperature" refers to the approximate average normal, internal temperature of the animal into which the composition is to be introduced, for example, about 37° C. in humans.

Physical properties of the compositions which make them useful for the augmentation of soft tissue are that they can be easily delivered, preferably by injection, to the desired tissue and that the composition is biocompatible and slowly bioabsorbed.

As used herein, the term "biocompatible" refers to compositions that are well tolerated by the body and which do not cause a prolonged adverse inflammatory reaction that would affect their function or performance.

As used herein, the term "bioabsorbable" refers to compositions which decomposes under normal in vivo physiological conditions into components which can be metabolized or excreted. "Slow bioabsorption" means that the composition performs the intended repair, augmentation, or viscosupplementation function for the appropriate time period, preferably longer than 1 month. In contrast, a material that is too quickly bioabsorbed requires frequent re-injection.

As used herein, the term "microdispersion" refers to a suspension of particles. The particles form a separate phase from that of the continuous phase. The particles may be in an amorphous or crystalline state. The particle size and concentration is chosen to provide the appropriate properties of the mixture. Typically, the particle size is on the order of 1 nm to 500 μm.

The compositions preferably can be easily injected using conventional techniques, that is, they can be injected manually, such as with a syringe and needle, preferably one having a 16 gauge diameter, more preferably having a 22 or larger gauge (i.e. smaller diameter needle).

In one embodiment, the PHA is a wax at room temperature (e.g., between 20 and 25° C.) which can be heated to body temperature or greater so that the composition liquefies, rendering it injectable. In a preferred embodiment, the PHA polymers are liquid polymers of polyhydroxyalkanoate copolymers which do not crystallize at body temperature, which bioabsorb slowly in vivo. Preferably, the material maintains at least half of its mass or molecular mass for a period over one year after implantation in vivo.

Sources of Polyhydroxyalkanoates

Polyhydroxyalkanoates (PHAs) are a class of naturally occurring polyesters that are synthesized by numerous organisms in response to environmental stress. For reviews, see Byrom, "Miscellaneous Biomaterials," in Byrom, ed., *Biomaterials* MacMillan Publishers, London, 1991, pp. 333–59; Hocking & Marchessault, "Biopolyesters" in Griffin, ed., *Chemistry and Technology of Biodegradable Polymers*, Chapman and Hall, London, 1994, pp. 48–96; Holmes, "Biologically Produced (R)-3-hydroxyalkanoate Polymers and Copolymers" in Bassett, ed., *Developments in Crystalline Polymers*, Elsevier, London, vol. 2, 1988, pp. 1–65; Lafferty et al., "Microbial Production of Poly-β-hydroxybutyric acid" in Rehm & Reed, eds., *Biotechnology*, Verlagsgesellschaft, Weinheim, vol. 66, 1988, pp. 135–76; Müller & Seebach, *Angew. Chem. Int. Ed. Engl.* 32:477–502 (1993); Steinbüchel, "Polyhydroxyalkanoic Acids" in Byrom, ed., *Biomaterials*, MacMillan Publishers, London, 1991, pp. 123–213; Williams & Peoples, CHEMTECH, 26:38–44, (1996), and the recent review by Madison & Husiman, *Microbiol. & Mol. Biol. Rev.* 63:21–53 (1999).

The PHA biopolymers may be broadly divided into three groups according to the length of their pendant groups and their respective biosynthetic pathways. Those with short pendant groups, such as polyhydroxybutyrate (PHB), a homopolymer of R-3-hydroxybutyric acid (R-3HB) units, are highly crystalline thermoplastic materials, and have been known the longest (Lemoigne & Roukhelman, *Annales des fermentations*, 5:527–36 (1925)). A second group of PHAs containing the short R-3HB units randomly polymerized with much longer pendant group hydroxy acid units were first reported in the early seventies (Wallen & Rohwedder, *Environ. Sci. Technol*, 8:576–79 (1974)). A number of microorganisms which specifically produce copolymers of R-3HB with these longer pendant group hydroxy acid units are also known and belong to this second group (Steinbüchel & Wiese, *Appl. Microbiol. Biotechnol.*, 37:691–97 (1992)). In the early eighties, a research group in The Netherlands identified a third group of PHAs, which contained predominantly longer pendant group hydroxy acids (De Smet, et al., *J. Bacteriol.*, 154:870–78 (1983)).

The PHA polymers may constitute up to 90% of the dry cell weight of bacteria, and are found as discrete granules inside the bacterial cells. These PHA granules accumulate in response to nutrient limitation and serve as carbon and energy reserve materials. Distinct pathways are used by microorganisms to produce each group of these polymers. One of these pathways leading to the short pendant group polyhydroxyalkanoates (SPGPHAs) involves three enzymes, namely thiolase, reductase and PHB synthase (sometimes called polymerase). Using this pathway, the homopolymer PHB is synthesized by condensation of two molecules of acetyl-Coenzyme A to give acetoacetyl-Coenzyme A, followed by reduction of this intermediate to R-3-hydroxybutyryl-Coenzyme A, and subsequent polymerization. The last enzyme in this pathway, namely the synthase, has a substrate specificity that can accommodate C3–C5 monomeric units including R-4-hydroxy acid and R-5-hydroxy acid units. This biosynthetic pathway is found, for example, in the bacteria *Zoogloea ramigera* and *Alcaligenes eutrophus*.

The biosynthetic pathway which is used to make the third group of PHAs, namely the long pendant group polyhydroxyalkanoates (LPGPHAs), is still partly unknown, however, it is currently thought that the monomeric hydroxyacyl units leading to the LPGPHAs are derived by the β-oxidation of fatty acids and the fatty acid pathway. The R-3-hydroxyacyl-Coenzyme substrates resulting from these routes are then polymerized by PHA synthases (sometimes called polymerases) that have substrate specificities favoring the larger monomeric units in the C6–C14 range. Long pendant group PHAs are produced, for example, by *Pseudomonads*.

Presumably, the second group of PHAs containing both short R-3HB units and longer pendant group monomers utilize both the pathways described above to provide the hydroxy acid monomers. The latter are then polymerized by PHA synthases able to accept these units.

In all about 100 different types of hydroxy acids have been incorporated into PHAs by fermentation methods so far (Williams, et. al., *Int. J. Biol. Macromol.*, 25:111–21 (1999)). Notably, these include PHAs containing functionalized pendant groups such as esters, double bonds, alkoxy, aromatic, halogens and hydroxy groups.

During the mid-1980's, several research groups were actively identifying and isolating the genes and gene products responsible for PHA synthesis. These efforts have lead to the development of transgenic systems for production of PHAs in both microorganism and plants, as well as enzymatic methods for PHA synthesis. Such routes could increase further the available PHA types. These advances have been reviewed in Williams & Peoples, CHEMTECH, 26:38–44 (1996), Madison & Huisman, *Microbiol. Mol. Biol. Rev.*, 63:21–53 (1999), and Williams & Peoples, Chem. Br. 33:29–32 (1997).

In addition to using biological routes for PHA synthesis, PHA polymers may also be derived by chemical synthesis. One widely used approach involves the ring-opening polymerization of β-lactone monomers using various catalysts or initiators such as aluminoxanes, distannoxanes, or alkoxy-zinc and alkoxy-aluminum compounds (see Agostini, et al., *Polym. Sci.*, Part A-1, 9:2775–87 (1971); Gross, et al., *Macromolecules,* 21:2657–68 (1988); Dubois, et al., *Macromolecules,* 26:4407–12 (1993); Le Borgne & Spassky, Polymer, 30:2312–19 (1989); Tanahashi & Doi, *Macromolecules,* 24:5732–33 (1991); Hori, et al., *Macromolecules,* 26:4388–90 (1993); Kemnitzer, et al., Macromolecules, 26:1221–29 (1993); Hori, et al., *Macromolecules,* 26:5533–34 (1993); Hocking & Marchessault, *Polym. Bull.,* 30:163–70 (1993); U.S. Pat. Nos. 5,489,470 and 5,502,116 to Noda). A second approach involves condensation polymerization of esters and is described in U.S. Pat. No. 5,563,239 to Hubbs, et al., and references therein. Researchers also have developed chemo-enzymatic methods to prepare PHAs. Xie et al., *Macromolecules,* 30:6997–98 (1997), for example, discloses a ring opening polymerization of beta-butyrolactone by thermophilic lipases to yield PHB.

The polyhydroxyalkanoates are also generally available in two physical forms, namely a latex form (Koosha, F. Ph.D. Dissertation, 1989, Univ. Nottingham, UK., *Diss. Abstr. Int. B* 51:1206 (1990)), and as a dry powder. Polyhydroxyalkanoates useful in the present compositions can be derived using any of the above methods, alone or in conjunction with the techniques described in the Examples below.

(i) Liquid Polymers

The polyhydroxyalkanoate liquid copolymers may contain varying amounts of the different hydroxy acid monomer types depending upon the specific properties that the liquid copolymer is desired to have. These polyhydroxyalkanoate polymers also may be blended with other polyhydroxyalkanoate polymers or other suitable materials prior to use.

In a preferred embodiment, the polymer is derived from one or more monomers selected from the group consisting of 2-hydroxybutanoate, 3-hydroxyalkanoates, 3-hydroxyalkenoates, 4-hydroxyalkanoates, 4-hydroxyalkenoates, 5-hydroxyalkanoates, 5-hydroxyalkenoates, 6-hydroxyalkanoates, and 6-hydroxyalkenoates. Preferred species include homopolymers and copolymers containing any combination of the monomers 3-hydroxybutyrate, 3-hydroxyvalerate, 3-hydroxypropionate, 2-hydroxybutyrate, 4-hydroxybutyrate, 4-hydroxyvalerate, 3-hydroxyhexanaote, 3-hydroxyheptanoate, 3-hydroxyoctanaote, 3-hydroxynonanoate, 3-hydroxydecanoate, 3-hydroxyundecanoate, 3-hydroxydodecanoate, 3-hydroxytridecanoate, 3-hydroxytetradecanoate, 3-hydroxypentadecanoate, 3-hydroxyhexadecanoate, 3-hydroxyheptadecanoate and 3-hydroxyoctadecanoate.

The viscosity of the liquid polyhydroxyalkanoate polymers may be varied by changing the molecular weight of the polymer, crosslinking, and/or by changing the composition of the polymers. The desired molecular weight may be achieved during the initial polymer synthesis, or alternatively adjusted up or down subsequently. Suitable methods for decreasing the molecular weight of polyhydroxyalkanoates, particularly to convert them from solid to liquid forms, include hydrolysis (particularly using acid catalysis), enzymatic degradation, irradiation, and mechanical or thermal treatments. Particularly desirable PHAs have relatively low molecular weights and are amorphous. Preferred PHA molecular weights are generally less than 100,000, preferably less than 50,000. Polyhydroxyalkanoates may be crosslinked by methods including the use of radical chemistry, irradiation, and with crosslinking agents. Representative methods are described in de Koning et al., *Polymer,* 35:2090–97 (1994); Gagnon, et al., *Polymer,* 35:4358–67 (1994); and Gagnon, et al., *Polymer,* 35:4368–75 (1994). Certain polyhydroxyalkanoates may also contain functionalities in their pendant groups such as unsaturation which can be a preferred site of crosslinking. Preferred polyhydroxyalkanoate polymer compositions will have viscosities high enough to prevent them from being dissolved in bodily fluids, but low enough to allow them to be easily injected.

A suitable viscosity would allow manual injection of the fluid through a 16 g needle, and a preferred viscosity would allow manual injection of the fluid through a 22 or smaller gauge needle. A suitable range of viscosity would be less than about 1,000,000 cP. The preferred range of viscosity varies from that of water (1 cP) to about that of molasses (100,000 cP). The viscosity of a fluid typically depends on the temperature, thus it is possible to adjust the viscosity of a fluid by varying its temperature. Typically viscosity of a material is lower at higher temperature. Prior to injection, the temperature of the fluid may be increased to facilitate injection. Depending upon the particle concentration, colloidal suspensions of PHA particles can be produced which have low viscosity (<100 000 cP). Absorption of the carrier fluid from the tissue can result in aggregation and potential coalescence of PHA particles. Depending on the composition and Mw, PHA polymers in the liquid form can be produced with higher viscosities (>100 000 cP). Prior to injection, the temperature of the liquid PHA may be increased to facilitate injection.

In addition to controlling viscosity by altering composition, molecular weight and using crosslinking, it is also possible to use these methods to control the rate of bioabsorption of the injectable polyhydroxyalkanoate in vivo. It is therefore possible to tailor bioabsorption rates to an application.

For medical or veterinary use, the PHA polymers may be sterilized, for example by gamma irradiation or by using ethylene oxide. Certain PHA polymers also may be sterilized in an autoclave with steam.

(ii) Polymer Microdispersions

In this embodiment of the compositions, suitable fluid carriers include liquid polyhydroxyalkanoates and aqueous solutions. Suitable polyhydroxyalkanoate particulates will have a diameter less than about 500 μm, preferably less than 50 μm, and most preferably less than about 5 μm.

The dispersed particles may be in a semi-crystalline or a fluid-like amorphous state. The amorphous state is preferred when aggregation and coalesce of the particle into larger particles is desired. Aggregation and coalescence is likely to be facilitated by absorption of the fluid carrier. Larger aggregates are often preferred as they are less likely to migrate from the site of injection. Larger or smaller particles may be preferred when surface area affects the bioabsorption profile.

Semicrystalline particles are preferred when the properties of the crystalline phase are desired. Semicrystalline particles are expected to have a longer absorption profile than analogous amorphous particles. Additionally, the diffusion of added agents (such as drugs or bioactive compounds) is affected by the crystalline state of the material. Diffusion of a drug out of a semicrystalline particle is typically slower than from an analogous amorphous particle. Thus, crystallinity may be adjusted to optimize the release of an added drug. A microdispersion may be preferred over a liquid polymer when low viscosity is desired. PHA microdispersions containing high solids concentration (>10% by weight solids) can be prepared which are suitable for injection. A liquid polymer would be preferred when the use of a carrier fluid is undesirable or when the polymer is intended to form a dense deposit.

Other Agents

The compositions may further include other agents to increase the safety and efficacy of the composition. Examples of such agents include compounds with antimicrobial activity anesthetics, adjuvants, anti-inflammatory compounds, surfactants, steroids, lipids, enzymes, antibodies, and hormones.

Other agents which can be included in the compositions include pharmacologically active or bioactive compounds, and dyes. Proteins and peptides can be included.

II. Applications for the Polyhydroxyalkanoate Compositions

The polyhydroxyalkanoate compositions may be administered anywhere in the body of animals where a bulking agent or viscosupplement is needed (e.g., intradermally, subcutaneously, intramuscularly and submucosally) in a therapeutic amount to provide the desired cosmetic, prosthetic, or pain-relieving effect. As used herein, the term "animal" includes mammals, preferably humans.

The compositions can be used for a variety of soft tissue repair and augmentation procedures, and as viscosupplements. For example, they can be used in facial tissue repair or augmentation including, but not limited to, camouflaging scars, filling depressions, smoothing out irregularities, correcting asymmetry in facial hemiatrophy, second branchial arch syndrome, facial lipodystrophy and camouflaging age-related wrinkles as well as augmenting facial eminences (lips, brows, etc.). Additionally, these compositions can be used to restore or improve sphincter function such as for treating stress urinary incontinence. Other uses include the treatment of vesicoureteral reflux by subureteric injection and application of these materials as general purpose fillers in the human body.

The compositions can be used a surgical aid.

In one embodiment, the compositions may be injected into skeletal tissues, such as bone, cartilage, tendons, and muscles. Such embodiments can be used to facilitate tissue repair or regeneration.

The compositions may also be used as viscosupplements, for example, to relieve pain due to osteoarthritis of the knee, in a similar manner to the commercial use of the product SYNVISC™. By directly injecting one of the presently described polyhydroxyalkanoate compositions into the knee joint, the material can act as a shock absorber and lubricant, providing prolonged relief from pain.

Representative surgical applications for the compositions include facial contouring (frown or glabellar line, acne scars, cheek depressions, vertical or perioral lip lines, marionette lines or oral commissures, worry or forehead lines, crow's feet or peri-orbital lines, deep smile lines or nasolabial folds, smile lines, facial scars, lips and the like); periurethral injection including injection into the submucosa of the urethra along the urethra, at or around the urethral-bladder junction to the external sphincter; ureteral injection for the prevention of urinary reflux; injection into the tissues of the gastrointestinal tract for the bulking of tissue to prevent reflux; to aid in sphincter muscle coaptation, internal or external, and for coaptation of an enlarged lumen; intraocular injection for the replacement of vitreous fluid or maintenance of intraocular pressure for retinal detachment; injection into anatomical ducts to temporarily plug the outlet to prevent reflux or infection propagation; larynx rehabilitation after surgery or atrophy; and any other soft tissue that can be augmented for cosmetic or therapeutic affect.

III. Methods and Devices for Administration of the Compositions

A variety of devices may be used for administering the compositions. A preferred method of administration uses a syringe and needle. Other suitable devices include the carpule device described in U.S. Pat. Nos. 4,664,655 and 4,758,234. Additional means may also be used to facilitate delivery of highly viscous polyhydroxyalkanoate compositions, such as the use of powered devices and devices which heat the polymer composition prior to delivery.

In one embodiment, the polyhydroxyalkanoate compositions are provided in the form of a kit including the polymeric materials in a reservoir along with delivery means, for example, a syringe or catheter.

The present invention will be further understood by reference to the following non-limiting examples.

EXAMPLE 1

Injectable Compositions of Polyhydroxyalkanoate 3836

PHA3836 (poly-3-hydroxyoctanoate-co-3-hydroxyhexanoate) (6.75 g, Mw 100,000), derived by microbial fermentation, was dissolved in dioxane (90 ml) containing 10 ml of concentrated hydrochloric acid. 1,3-Butanediol (2.5 ml) was added and the mixture was heated to reflux. Samples (5 ml) were removed periodically and dried by rotary evaporation. The molecular mass of these products were determined by GPC analysis, see Table 1. Lower molecular weight compositions of PHA3836 were found to be suitable for injection as viscous fluids, particularly after heating prior to injection.

TABLE 1

Molecular Weight Analysis of Acid Alkoholysis Products of PHA3836

| Reaction Time (min.) | Mw[a] | Mw/Mn[a] |
|---|---|---|
| 0 | 103000 | 2.7 |
| 20 | 29000 | 1.8 |
| 40 | 7400 | 1.6 |
| 60 | 4700 | 1.7 |
| 80 | 2900 | 1.5 |
| 100 | 2600 | 1.5 |
| 120 | 2000 | 1.5 |
| 180 | 1500 | 1.5 |
| 240 | 1200 | 1.4 |

[a]Determined by GPC analysis. Isolated polymers were dissolved in chloroform at approximately 1 mg/mL and samples (50 μL) were chromatographed on a Waters Stryagel HT6E column at a flow rate of 1 mL chloroform per minute at room temperature using a refractive index detector. Molecular masses were determined relative to polystyrene standards of narrow polydispersity.

EXAMPLE 2

Injectable Polyhydroxyalkanoate 3836 Compositions

PHA3836 (20.0 g, Mw 100,000) was dissolved in dioxane (250 ml) with heating. After complete dissolution, concentrated hydrochloric acid (20 ml) and 1,3-butanediol (10 g) were added. The mixture was heated to reflux. Samples (100 ml) were removed at 10 minutes and 30 minutes, samples A and B, respectively. Solvent was removed by rotary evaporation followed by lyophilization. The molecular mass of these products were determined by GPC analysis, see Table 2. Upon standing at room temperature, samples A and B solidified into elastic, waxy materials. After heating to 50° C., these waxy materials became viscous fluids suitable for injection. After cooling to room temperature, products A and B remained viscous fluids.

TABLE 2

Molecular Weight Analysis of Acid Alcoholysis Products of PHA3836

| Sample | Reaction Time (min.) | Mw[a] | Mw/Mn[a] |
|---|---|---|---|
| A | 10 | 60000 | 2.0 |
| B | 30 | 20000 | 1.8 |

[a]Determined by GPC analysis, see Table 1 for GPC conditions.

EXAMPLE 3

Injectable Polyhydroxyalkanoate 3836 Compositions

PHA3836 (30.0 g, Mw 100,000) was dissolved in dioxane (200 ml) with heating. After complete dissolution, concentrated hydrochloric acid (20 ml) was added and the mixture was heated to reflux for 40 minutes. After cooling to room temperature, solid sodium bicarbonate was added to neutralize the acid. Solid $MgSO_4$ was added to remove water. The mixture was filtered to remove solids and concentrated to yield the oligomeric PHA3836 (27 g, yield 90%). This material was designated as sample C. The molecular mass of this product was determined to be 15,000 by GPC analysis, see Table 1 for GPC conditions. Upon standing at room temperature, sample C became an elastic, waxy material. After heating to 50° C., the wax became a viscous fluid suitable for injection.

EXAMPLE 4

Injectable Polyhydroxyalkanoate 3400 Compositions

PHA3400 (poly-3-hydroxybutyrate) was dissolved in glacial acetic acid by heating at reflux with overhead stirring to yield a 6% solution. After complete dissolution of PHA3400, water (15% of the acetic acid volume) was added to yield a clear solution. Initially, the solution is viscous, however, with time the viscosity decreases as the Mw of the polymer is reduced. The solution was stirred at reflux (108° C.). At various times, aliquots (3 ml) were removed and were precipitated into water (10 ml). The precipitate was collected via filtration, washed with water, dried and analyzed. The precipitate was weighed to determine the amount of precipitated material. The yields of recoverable material were typically >60%, thus a significant portion of PHA3400 may be soluble in the acetic acid/water solution after precipitation of the polymer. The Mw of the polymer was analyzed by GPC, using a column which is designed for the analysis of low Mw polymers (500 000–500 g/mol, Waters HR4E). The analysis was performed in chloroform (1 ml/min, RI detector, ambient temp., polystyrene standards), see Table 3.

The hydrolysis of PHA3400 in 85% acetic acid at reflux (108° C.) proceeds smoothly with reasonable recovery of product (>60%). A plot of log Mw versus log Reaction Time is linear, thus one can optimize the process to yield polymer of desired Mw and viscosity by varying the reaction time. There is no crotonization of the polymer and the resultant product is partially terminally acetylated, as evidenced by the acetyl resonance in the $^1$H NMR spectrum. Under the conditions used, polymer of 8,000 g/mol can be produced in 4 hours and 1,500 g/mol (Mw/Mn=1.32) can be produced in about 23 hours.

In general the PHA3400 oligomers are semi-crystalline at room temperature. These materials can be melt or solution mixed with a variety of other biocompatible materials or solvents to yield viscous fluids at body temperature that are suitable for injection into soft tissue.

TABLE 3

Data for PHA3400 hydrolysis in 85% Acetic Acid

| Reflux time (hr) | Mass (mg) | Yield % | Mw |
|---|---|---|---|
| 0 | 137 | 80 | 354,000 |
| 1 | 69 | 40 | |
| 2 | 102 | 59 | 16,000 |
| 4 | 108 | 63 | 8,000 |
| 8 | 118 | 69 | 4,400 |
| 23 (end) | 9.5g | 60 | 1,500 |

EXAMPLE 5

Injectable Polyhydroxyalkanoate 4400 Compositions

Dissolve PHA4400 (poly-4-hydroxybutyrate, 8.5 g, Mw 430,000) in anhydrous THF (280 ml) to produce 3% wt./vol. solution. Apply gentle heating to 60° C. to facilitate dissolution of the polymer. Slowly add 1 ml of absolute ethanol. Cool solution to room temperature. Add aliquots of sodium methoxide (0.1 M in methanol) to provide desired Mw and viscosity of the product (see Table 4). Stir at room temperature for 10 minutes. Quench reaction with acid (if desired). Filter and evaporate THF to yield product (7.5 g, for 300 μL added sodium methoxide).

In general the PHA4400 oligomers are semi-crystalline at room temperature. These materials can be melt or solution mixed with a variety of other biocompatible materials or solvents to yield viscous fluids at body temperature that are suitable for injection into soft tissue.

TABLE 4

Data for PHA4400 Hydrolysis

| Amount added MeONa (μL) | GPC Ret. Time (min.) | Molecular Mass[b] |
|---|---|---|
| O (starting material) | 7.87 | 430,000 |
| 100 | 8.0 | 320,000 |
| 200 | 8.6 | 82,000 |
| 300 | 9.1 | 25,000 |

[b]Log Mw = GPC Ret. Time * (−0.984) + 13.376, determined relative to polystyrene.

EXAMPLE 6

Injectable Polyhydroxyalkanoate 3444 Compositions

PHA3444 (poly-3-hydroxybutyrate-co-4-hydroxybutyrate) copolymers were prepared in recombinant *E. coli*.

The polymers were extracted from the dried biomass with chloroform and precipitated into 3–5 volumes of methanol. The material properties of these copolymers can be varied depending on the monomeric composition of polymers, see Table 5. Copolymers containing greater than 10% 4-hydroxybutyrate (4HB) were elastic and rubbery. Samples containing 30–35% 4-hydroxybutyrate were of low crystallinity as demonstrated by low DH, and were slow to recrystallize from the melt.

In general the PHA3444 oligomers are semi-crystalline at room temperature. The amount of crystallinity can be adjusted by varying the composition. These materials can be melt or solution mixed with a variety of other biocompatible materials or solvents to yield viscous fluids at body temperature that are suitable for injection into soft tissue.

TABLE 5

Properties of PHA3444 Copolymers Produced in Recombinant *E. coli*

| % 4HB | DH (J/g) | Tg (° C.) | Mw (by GPC) |
|-------|----------|-----------|-------------|
| 12    | 60       | −7        | 760,000     |
| 15    | 44       | −10       | 830,000     |
| 32    | 10       | −20       | 800,000     |

Modifications and variations of the compositions and methods of use will be obvious to those skilled in the art from the foregoing detailed description and are intended to come with the following claims.

What is claimed is:

1. A composition for the repair or augmentation of tissue in animal or human, comprising:
   a biocompatible, bioabsorbable fluid which comprises a polyhydroxyalkanoate which is injectable into a human or animal for repair or augmentation of tissue,
   wherein the polyhydroxyalkanoate is a liquid or wax at a temperature between about 20 and 25° C. or wherein the polyhydroxyalkanoate is liquid at the body temperature of the animal.

2. The composition of claim 1 wherein the polyhydroxyalkanoate is a liquid at about 37° C.

3. The composition of claim 1 wherein the biocompatible fluid is a microdispersion of particles of the polyhydroxyalkanoate dispersed in a physiologically compatible liquid carrier.

4. The composition of claim 3 wherein the carrier is a second polyhydroxyalkanoate or an aqueous solution.

5. The composition of claim 1 wherein the particles have a diameter of less than about 500 μm.

6. The composition of claim 5 wherein the diameter is less than about 50 μm.

7. The composition of claim 6 wherein the diameter is less than about 5 μm.

8. The composition of claim 1 wherein the polymer derived from one or more monomers selected from the group consisting of 2-hydroxybutanoate, 3-hydroxyalkanoates, 3-hydroxyalkenoates, 4-hydroxyalkanoates, 4-hydroxyalkenoates, 5-hydroxyalkanoates, 5-hydroxyalkenoates, 6-hydroxyalkanoates, and 6-hydroxyalkenoates.

9. The composition of claim 1 wherein the polyhydroxyalkanoate has a molecular weight of less than 100,000 as determined by gel permeation chromatography.

10. The composition of claim 9 wherein the molecular weight is less than 50,000 as determined by gas permeation chromatography.

11. The composition of claim 1 having a viscosity of between about 1 and 100,000 cP.

12. The composition of claim 11 having a viscosity of between about 1 and 10,000 cP.

13. The composition of claim 1 further comprising a bioactive agent.

14. The composition of claim 1 further comprising a peptide or protein.

15. The composition of claim 1 wherein the polyhydroxyalkanoate is amorphous.

16. A composition suitable for use in the treatment of osteoarthritic knees comprising:
   a biocompatible, bioabsorbable fluid which comprises a polyhydroxyalkanoate, wherein the composition is suitable for use as a viscosupplement,
   wherein the polyhydroxyalkanoate is a liquid or wax at a temperature between about 20 and 25° C. or wherein the polyhydroxyalkanoate is liquid at the body temperature of the animal.

17. A kit comprising
   (a) the composition of claim 1; and
   (b) a means for delivering the composition to a patient.

18. The kit of claim 17 wherein the means for delivering comprises a needle and a syringe.

* * * * *

UNITED STATES PATENT AND TRADEMARK OFFICE
CERTIFICATE OF CORRECTION

| | | |
|---|---|---|
| PATENT NO. | : 7,025,980 B1 | Page 1 of 1 |
| APPLICATION NO. | : 09/661773 | |
| DATED | : April 11, 2006 | |
| INVENTOR(S) | : Simon F. Williams and David P. Martin | |

It is certified that error appears in the above-identified patent and that said Letters Patent is hereby corrected as shown below:

Column 11, line 38, replace "25°C." with --25°C--.
Column 12, line 9, insert --is-- after "polymer".
Column 12, line 37, replace "25°C." with --25°C--.

Signed and Sealed this

Fourth Day of September, 2007

JON W. DUDAS
*Director of the United States Patent and Trademark Office*